(12) United States Patent
Alam

(10) Patent No.: US 10,207,123 B2
(45) Date of Patent: Feb. 19, 2019

(54) SKULL IMPLANTED MAGNET ASSEMBLY FOR BRAIN STIMULATION

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Imran Khurshid Alam, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 261 days.

(21) Appl. No.: 15/251,402

(22) Filed: Aug. 30, 2016

(65) Prior Publication Data
US 2018/0056084 A1    Mar. 1, 2018

(51) Int. Cl.
*A61N 2/06* (2006.01)
*A61N 2/00* (2006.01)

(52) U.S. Cl.
CPC .............. *A61N 2/06* (2013.01); *A61N 2/008* (2013.01)

(58) Field of Classification Search
CPC .................................. A61N 2/008; A61N 2/06
See application file for complete search history.

(56) References Cited

U.S. PATENT DOCUMENTS

| | | | |
|---|---|---|---|
| 4,612,915 A | 9/1986 | Hough et al. | |
| 5,135,466 A | 8/1992 | Fedorov et al. | |
| 5,389,981 A | 2/1995 | Riach, Jr. | |
| 5,611,689 A | 3/1997 | Stemmann | |
| 5,817,000 A | 10/1998 | Souder | |
| 6,032,677 A | 3/2000 | Blechman et al. | |
| 6,306,076 B1 | 10/2001 | Gill | |
| 6,461,288 B1 | 10/2002 | Holcomb | |
| 6,488,617 B1 | 12/2002 | Katz | |
| 6,932,607 B2 | 8/2005 | Honkura et al. | |
| 6,991,594 B2 | 1/2006 | Holcomb | |
| 7,198,596 B2 | 4/2007 | Westerkull | |
| 8,029,570 B2 | 10/2011 | Barnes et al. | |

(Continued)

FOREIGN PATENT DOCUMENTS

| CN | 85 2 04378 U | 1/1987 |
|---|---|---|
| CN | 2582652 Y | 10/2003 |

(Continued)

OTHER PUBLICATIONS

"Cochlear™ Baha® System Products", http://www.cochlear.com/wps/wcm/connect/us/for-professionals/products/baha/products, Jun. 17, 2016, 2 pages.

*Primary Examiner* — Christine H Matthews
(74) *Attorney, Agent, or Firm* — Oblon, McClelland, Maier & Neustadt, L.L.P.

(57) ABSTRACT

A skull-implantable magnet assembly for delivering a static magnetic field to a patient's brain, comprising a rod-shaped magnet housed within a skull screw, removably attached to a casing housing at least one flat magnet, is described. Details of the exterior construction are discussed, as well as magnet arrangements and methods of treating a brain tumor or neurological ailment of a patient.

15 Claims, 13 Drawing Sheets

(56) References Cited

U.S. PATENT DOCUMENTS

| | | |
|---|---|---|
| 8,585,568 B2 | 11/2013 | Phillips et al. |
| 8,585,569 B2 | 11/2013 | Holcomb |
| 9,319,810 B2 | 4/2016 | Leigh et al. |
| 9,352,149 B2 | 5/2016 | Thenuwara et al. |
| 2005/0165458 A1 | 7/2005 | Boveja et al. |
| 2007/0053536 A1 | 3/2007 | Westerkull |
| 2007/0083237 A1 | 4/2007 | Teruel |
| 2013/0281764 A1 | 10/2013 | Björn et al. |
| 2014/0276182 A1 | 9/2014 | Helekar et al. |
| 2018/0160242 A1* | 6/2018 | Sriskandarajah .... H04R 25/606 |

FOREIGN PATENT DOCUMENTS

| | | |
|---|---|---|
| EP | 2 795 927 B1 | 4/2016 |
| WO | WO 2011/135136 A1 | 11/2011 |

* cited by examiner

SKULL IMPLANTED MAGNET ASSEMBLY FOR BRAIN STIMULATION

BACKGROUND OF THE INVENTION

Technical Field

The present invention relates to a magnet assembly comprising a magnetic screw configured to traverse a patient's skull to stimulate the patient's brain with a static magnetic field, and methods of use.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Transcranial magnetic stimulation has been suggested as a possible therapeutic tool in treating superficial cortical tumors and relieving vascular spasm and depression. In behavioral models of depression, magnetic stimulation has induced similar effects to those of electroconvulsive shock. There is an extensive body of clinical data demonstrating the safety and effectiveness of magnetic stimulation of the brain in treating major depression in patients—especially those who have not received benefit from antidepressant medication.

Repetitive transcranial magnetic stimulation (rTMS) uses a magnet instead of an electrical current to activate the brain. First developed in 1985, rTMS has been studied as a possible treatment for depression, psychosis, and other disorders since the mid-1990's.

Unlike electroconvulsive therapy (ECT), in which electrical stimulation is more generalized, rTMS can be targeted to a specific site in the brain. Scientists believe that focusing on a specific spot in the brain reduces the chance for the type of side effects that are associated with ECT. But opinions vary as to what spot is best.

A typical rTMS session lasts 30 to 60 minutes and does not require anesthesia. An electromagnetic coil is held against the forehead near an area of the brain that is thought to be involved in mood regulation. Then, short electromagnetic pulses are administered through the coil. The magnetic pulse easily passes through the skull, and causes small electrical currents that stimulate nerve cells in the targeted brain region. And because this type of pulse generally does not reach further than two inches into the brain, scientists can select which parts of the brain will be affected and which will not be. The magnetic field is about the same strength as that of a magnetic resonance imaging (MRI) scan. Generally, the person will feel a slight knocking or tapping on the head as the pulses are administered. FIG. 1 illustrates a patient undergoing rTMS.

Sometimes a person may have discomfort at the site on the head where the magnet is placed. The muscles of the scalp, jaw, or face may contract or tingle during the procedure. Mild headache or brief lightheadedness may result. It is also possible that the procedure could cause a seizure, although documented incidences of this are uncommon. A recent large-scale study on the safety of rTMS found that most side effects, such as headaches or scalp discomfort, were mild or moderate, and no seizures occurred. Because the treatment is new, however, long-term side effects are unknown.

Not all scientists agree on the best way to position the magnet on the patient's head or give the electromagnetic pulses. They also do not yet know if rTMS works best when given as a single treatment or combined with medication. More research, including a large NIMH-funded trial, is underway to determine the safest and most effective use of rTMS.

Clinical trials studying the effectiveness of rTMS reveal mixed results. When compared to a placebo or inactive (sham) treatment, some studies have found that rTMS is more effective in treating patients with major depression. But other studies have found no difference in response compared to inactive treatment.

Electric stimulation of a patient's brain may be combined with rTMS. For example, FIG. 2 shows that the cerebral motor cortex can be stimulated with a magnetic stimulating coil and with a direct current delivered by implanted electrodes. These two stimulation therapies can produce compound muscle action potentials by triggering the correct neuronal pathways.

In 2008, rTMS was approved for use by the FDA as a treatment for major depression for patients who have not responded to at least one antidepressant medication. It is also used in countries such as Canada and Israel as a depression treatment for patients who have not responded to medications and who might otherwise be considered for ECT ["Brain Stimulation Therapies," The National Institute of Mental Health, 2016—incorporated herein by reference in its entirety].

Magnetic seizure therapy (MST) borrows certain aspects from both electroconvulsive therapy (ECT) and rTMS. Like rTMS, it uses a magnetic pulse instead of electricity to stimulate a precise target in the brain. However, unlike rTMS, MST aims to induce a seizure like ECT. So the pulse is given at a higher frequency than that used in rTMS. Therefore, like ECT, the patient must be anesthetized and given a muscle relaxant to prevent movement. The goal of MST is to retain the effectiveness of ECT while reducing the cognitive side effects usually associated with ECT.

MST is currently in the early stages of testing, but initial results are promising. Studies on both animals and humans have found that MST produces fewer memory side effects, shorter seizures, and allows for a shorter recovery time than ECT. However, its effect on treatment-resistant depression is not yet established. Studies are underway to determine its antidepressant effects ["Brain Stimulation Therapies," The National Institute of Mental Health, 2016—incorporated herein by reference in its entirety].

The market for neuro-technology products is poised to become one of the most dramatic growth areas of the 21st Century. Spurred on by medical developments and discoveries that cure disease, alleviate suffering, and generally improve the quality of life, many leading research institutions and healthcare firms have gained the world's attention and respect in recent years. Within biomedical technology, the field of neuro-technology stands out for its promise of restoring human brain function, and for transferring biomedical concepts and processes to the industrial and information processing sectors.

The fields of neuro-technology and neuroscience offer the promise of generating significant capital interest and funding, despite the current depressed state of new technology ventures. Investors will be looking for new opportunities in markets related to neuroscience. Neuro-technology, with its promise and proven record at such tasks as restoring hearing to deaf patients and hand function to quadriplegics, offers a clear opportunity.

In view of the forgoing, one objective of the present invention is to provide an implantable magnet assembly for stimulating a patient's brain with a static magnetic field.

BRIEF SUMMARY OF THE INVENTION

According to a first aspect, the present disclosure relates to an implantable magnet assembly comprising a rod-shaped magnet housed within a skull screw. The skull screw has a head end and a point end and is configured to traverse a patient's skull with the point end located at the interior surface of the skull and the head end located at the exterior surface of the skull. The implantable magnet assembly also comprises a casing removably attached to the head end of the skull screw, with the casing housing at least one flat magnet and arranged substantially perpendicularly with the rod-shaped magnet.

In one embodiment, the implantable magnet assembly emits a magnetic field with a magnetic field strength of 2 mT-15 T as measured on an exterior surface.

In one embodiment, the implantable magnet assembly has one flat magnet which is cylindrically-shaped and aligned concentrically with the rod-shaped magnet with like magnetic poles of both magnets facing the same direction.

In one embodiment, the implantable magnet assembly has at least two flat magnets with edges arranged side-by-side in the casing.

In a further embodiment, where the implantable magnet assembly has at least two flat magnets with edges arranged side-by-side in the casing, not every flat magnet is arranged with magnetic poles facing in the same direction.

In another embodiment, where the implantable magnet assembly has at least two flat magnets with edges arranged side-by-side in the casing, all of the flat magnets are arranged with their magnetic poles in the same direction as the magnetic pole of the rod-shaped magnet.

In another embodiment, the exterior of the skull screw of the implantable magnet assembly is at least one of titanium, titanium alloy, stainless steel, cobalt alloy, magnetite, ferrite alloy, neodymium alloy, samarium alloy, Alnico, carbon fiber, polyethylene, polymethylmethacrylate, polyether ether ketone, or polycarbonate.

In another embodiment, the exterior surface of the casing comprises a tab portion, a notch, or a textured surface to facilitate a finger grip.

In another embodiment, the implantable magnet assembly has a fastening mechanism which may be a bayonet mount, a threaded connector, a clutch, a latch, a key and keyhole, a tongue and groove joint, a snap fastener, an R-clip, or a clamp, which is configured to removably attach the casing to the head end of the skull screw.

In another embodiment, the implantable magnet assembly also has a strap with a recess to receive the casing, wherein the strap secures the casing in place when encircling a part of the patient's head.

In one embodiment, the implantable magnet assembly includes a cushion on a bottom portion of the casing that receives the head end of the skull screw in order to cushion a head of a patient.

In one embodiment, the casing of the implantable magnet assembly comprises an indentation in the central portion on the side closest to the patient's head in order to receive the head end of the skull screw.

According to a second aspect, the present disclosure relates to a method of delivering a static magnetic field to a patient's brain by implanting the implantable magnet assembly into the patient's skull wherein the skull screw traverses the patient's skull with the point end located at the interior surface of the skull and the head end located at the exterior surface of the skull.

In one embodiment of the method, the static magnetic field is delivered for more than 2 hours.

In one embodiment of the method, the cognitive performance of the patient is increased relative to a second patient not receiving a magnetic field from a magnet or an electromagnet.

In one embodiment of the method, the patient has a brain tumor and/or a neurological ailment, and the brain tumor and/or the neurological ailment is treated.

In one embodiment of the method, where a neurological ailment of the patient is treated, the neurological ailment is epilepsy, migraine, depression, anxiety, attention deficit disorder, hyperactivity, bipolar disorder, stroke, dementia, schizophrenia, delirium, neurosis, psychosis, Parkinson's disease, alcohol withdrawal, drug withdrawal, dizziness, motion sickness, insomnia, dystonia, chronic pain, obsessive compulsive disorder, Tourette's syndrome, essential tremor, spasticity, trigeminal neuralgia, and/or headache.

In a further embodiment of the method, the method additionally involves removing the casing while leaving the rod-shaped magnet and skull screw in place and attaching a second casing with at least one second flat magnet, wherein the at least one second flat magnet applies a magnetic field that differs from the magnetic field produced by the at least one flat magnet.

According to a third aspect, the present disclosure relates to a method of delivering a static magnetic field to a brain of a patient which involves implanting an implantable magnet into the patient's skull. This implantable magnet is a rod-shaped magnet housed within a skull screw, with the skull screw having a head end and a point end. When implanted, the skull screw traverses the patient's skull with the point end located at the interior surface of the skull and the head end located at the exterior surface of the skull.

In one embodiment of the method, the patient has a brain tumor and/or a neurological ailment, and the brain tumor and/or neurological ailment of the patient is treated.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Embodiments of the present disclosure will now be described more fully hereinafter with reference to the accompanying drawings, in which some, but not all embodiments of the disclosure are shown.

According to a first aspect, the current disclosure describes an implantable magnetic assembly that includes a rod-shaped magnet housed within a skull screw. The skull screw has two ends, a point end and a head end, and is configured to traverse a patient's skull with the point end located at the interior surface of the skull, towards the brain, with the head end located at the exterior surface of the skull. Preferably the top of the skull screw head end is located at least 3 mm, preferably at least 4 mm, more preferably at least 5 mm above the scalp of the patient. Preferably, the point end of the skull screw does not physically contact or perturb the brain tissue. In an alternative embodiment, the skull screw is inserted sufficiently deep that the top of the skull screw head end is at the same level as the patient's skull or scalp, or between those two levels.

Figure 4:
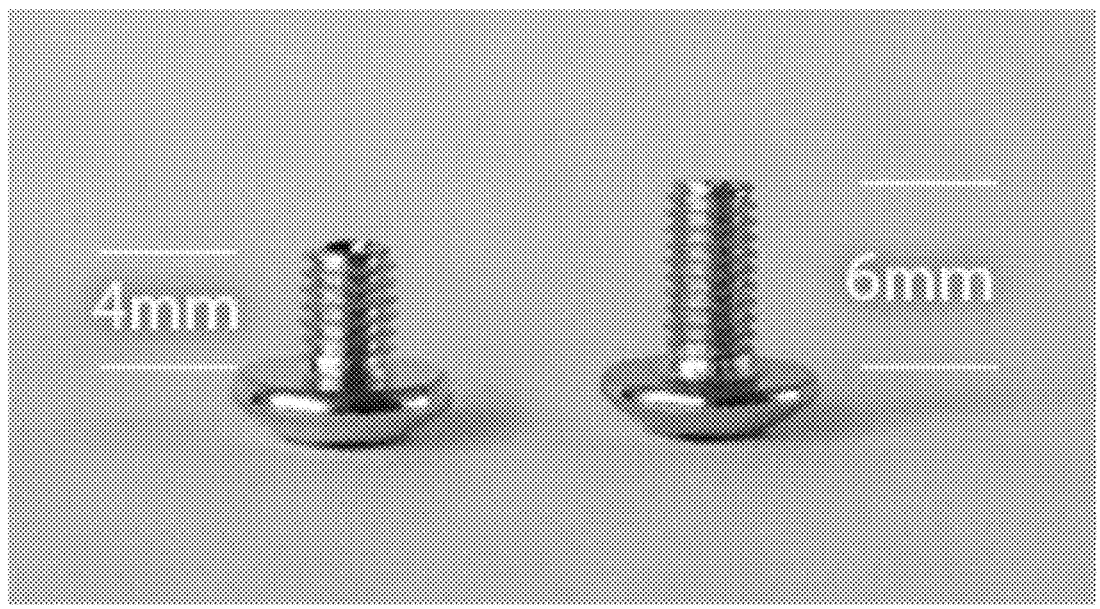
FIG. 4 is an example of skull screws with 4 mm and 6 mm shaft lengths.

In one embodiment, the skull screw may comprise along its length an unthreaded head section and a shaft section, wherein the unthreaded head section is located near the head end, and the shaft section is located near the point end and may be fully or partially threaded. The length of the unthreaded head section may be 1-10 mm, preferably 2-8 mm, more preferably 3-7 mm. The skull screw shaft section may have a total length of 3-10 mm, preferably 4-9 mm, more preferably 5-8 mm. FIG. 4 shows skull screws with a completely threaded shaft sections of 4 mm and 6 mm in length. In the embodiment where the shaft section is partially threaded, there may be a threaded section near the point end and an unthreaded section between the threaded section and the unthreaded head section. The unthreaded section may comprise less than 50%, preferably less than 20%, more preferably less than 10% of the length of the shaft section. In one embodiment there is no unthreaded head section, so the length of the screw is completely threaded, such as the skull screw in FIG. 5A. In an alternative embodiment, the shaft section is completely unthreaded, similar to a nail. The shaft section may be cylindrical, or conical with a taper towards the point end. The core diameter, which is the smallest diameter of the threaded section, may be 0.5-9 mm, preferably 0.8-8 mm, more preferably 1-7 mm. The thread diameter, which is the widest diameter of the threaded section, may be 1-10 mm, preferably 1.2-9 mm, more preferably 1.5-8 mm. The shaft section diameter may be 0.5-9 mm, preferably 0.8-8 mm, more preferably 1-7 mm. The core diameter may vary along the length of the shaft section. For example, the core of the screw may be conical while the threaded diameter is cylindrical.

In one embodiment, the exterior of the skull screw may comprise or be made of titanium, titanium alloy, stainless steel, cobalt alloy, magnetite, ferrite alloy, neodymium alloy, samarium alloy, Alnico, carbon fiber, polyethylene, polymethylmethacrylate, polyether ether ketone, polycarbonate, and/or some other biocompatible material. Preferably, the skull screw may be comprised of a titanium alloy. To increase biocompatibility, the exterior of the skull screw may be anodized or texturized. Alternatively, an ion beam of calcium, potassium, hydroxyapatite, magnesium, nitrogen, and/or argon ions may be used to deposit or implant those ions on the exterior of the skull screw. Similarly, the threads and/or exterior surface of the screw may be coated with a material to reduce friction, such as polytetrafluoroethylene (PTFE) and/or ultra-high-molecular-weight polyethylene (UHMWPE). In one embodiment, the skull screw comprises materials that can withstand sterilization by autoclaving.

The thread may be single or double start and may be right-handed or left-handed. The design of the screw thread may allow for an implanted screw to be self-locking, self-tapping, and/or self-drilling. In a preferred embodiment, the skull screw may have a lower pullout strength compared to a conventional bone and/or skull screw. The shape of the screw threads may be V, American National, British Standard, buttress, Unified Thread Standard, ISO metric, or some different shape known to those of ordinary skill. The pitch of the thread may be 0.1 mm-1 mm, preferably 0.2-0.9 mm, more preferably 0.2-0.8 mm. The point end of the skull screw may be pointed, flat, curved, beveled, or some other shape. FIGS. 5A, 5B, 6A, and 6B show skull screws with beveled point ends. FIG. 4 shows skull screws with flat ends.

In one embodiment, the skull screw shaft section may comprise at least two threaded sections separated by an unthreaded section. The at least two threaded sections may have the same dimensions or they may differ in length, thread diameter, and/or core diameter. In one embodiment, at least two threaded sections are adjacent on the shaft section and differ by thread diameter, and/or core diameter. Alternatively, the shaft section may comprise at least two unthreaded sections separated by a threaded section.

Figure 5A:
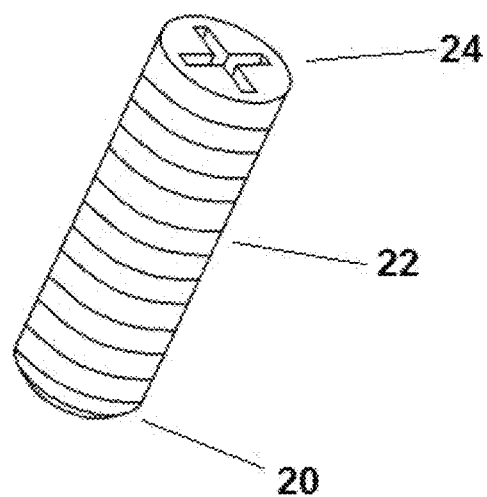
FIG. 5A is an example of a magnet-containing skull screw.
Figure 5B:
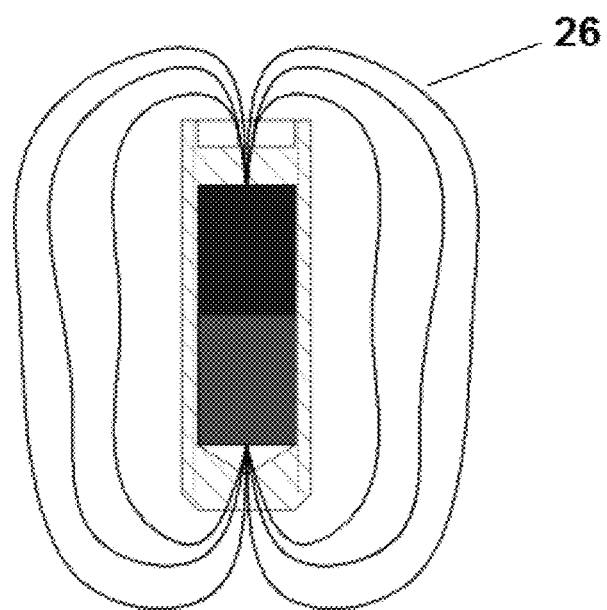
FIG. 5B is a cross-section view of the skull screw in FIG. 5A showing the magnet and magnetic field.

FIG. 5A shows a skull screw without an unthreaded head section but with a head end 24, a fully threaded shaft section 22, and a point end 20. Where a skull screw comprises an unthreaded head section, the widest diameter of the unthreaded head section may be greater than the core diameter of the screw by more than 1 mm, preferably more than 2 mm, more preferably more than 2.5 mm. In alternative embodiments, the widest diameter of the unthreaded head section may be equal to or less than the core diameter, for example, the widest diameter of the unthreaded head section may be smaller than the core diameter by 2.5 mm or less, preferably 2 mm or less, more preferably 1 mm or less. The unthreaded head section of the skull screw may be shaped cylindrically, or may be a right prism with a regular polygonal base such as a square, a hexagon, or octagon, or it may be some other shape, such as a sphere or hemisphere.

In one embodiment, the screw has a hollow core in which to receive a rod-shaped magnet. This hollow core may start from the head end of the skull screw and terminate before the point end of the skull screw. The hollow core may have a length that is 50-99%, preferably 60-97%, more preferably 70-95% of the total length of the screw. The hollow core diameter may be 0.75 mm-8.75 mm, preferably 2-8 mm, more preferably 3-7 mm. Preferably, the diameter of the hollow core is nearly the diameter of a cylindrical rod-shaped magnet, but just large enough to allow air to escape when inserting the magnet. Alternatively, a groove or channel may be machined into a side of the hollow core lengthwise to allow air to escape. Alternatively, the hollow core may be a different shape than the rod-shaped magnet. For example, the hollow core may be a rectangular prism while the rod-shaped magnet is a cylinder, or vice versa. The rod-shaped magnet may have a length that is 50-99%, preferably 60-97%, more preferably 70-95% of the total length of the hollow core. However, in one embodiment, the rod-shaped magnet has a length that is longer than the hollow core and the magnet protrudes above the head end of the skull screw.

In one alternative embodiment, the screw is cannulated, meaning that the length of the hollow core equals the length of the screw. In another alternative embodiment, the hollow core starts from the point end of the screw and ends before the head end.

As used herein, "rod-shaped" refers to a right prism or cylinder shape wherein the height of the prism or cylinder is larger than its largest width. In one embodiment, the rod-shaped magnet is a prism with a cylindrical shape, wherein a cylindrical rod-shaped magnet has a height greater than its diameter.

In one embodiment, the rod-shaped magnet is inserted into and then permanently sealed within the skull screw, such as by welding or an adhesive. In another embodiment, the rod-shaped magnet is inserted and then secured in place by an adhesive, a solder, a plug, or a cap. The plug or cap may be secured into the head end of the skull screw by adhesive or solder or may be fastened by a fastening mechanism such as screw threads or a latch. The fastening mechanism may be on the outside surface of the skull screw or within the skull screw. In one embodiment, the skull screw is made of a ferromagnetic material, and the rod-shaped magnet is secured by magnetic attraction. In one embodiment, the skull screw may remain in a patient's skull while the rod-shaped magnet is removed and replaced with a different rod-shaped magnet.

Figure 1:
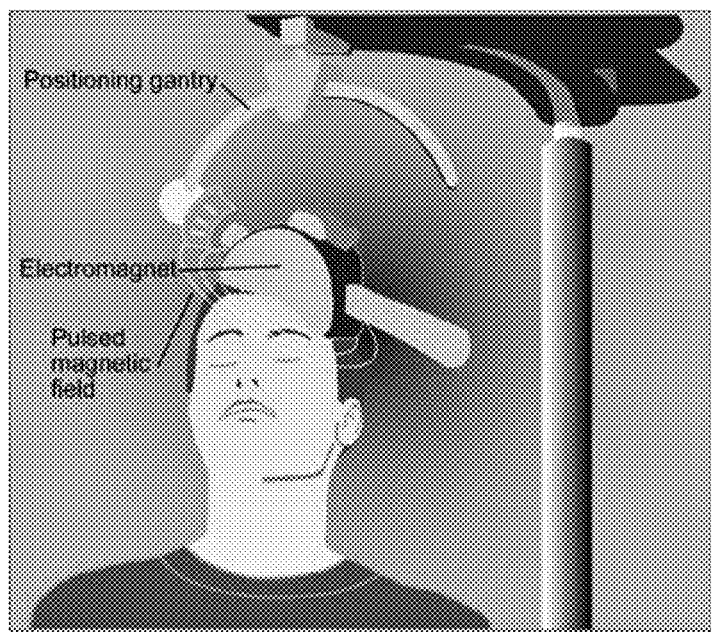
FIG. 1 is an illustration of a patient receiving repetitive transcranial magnetic stimulation (rTMS).
Figure 2:
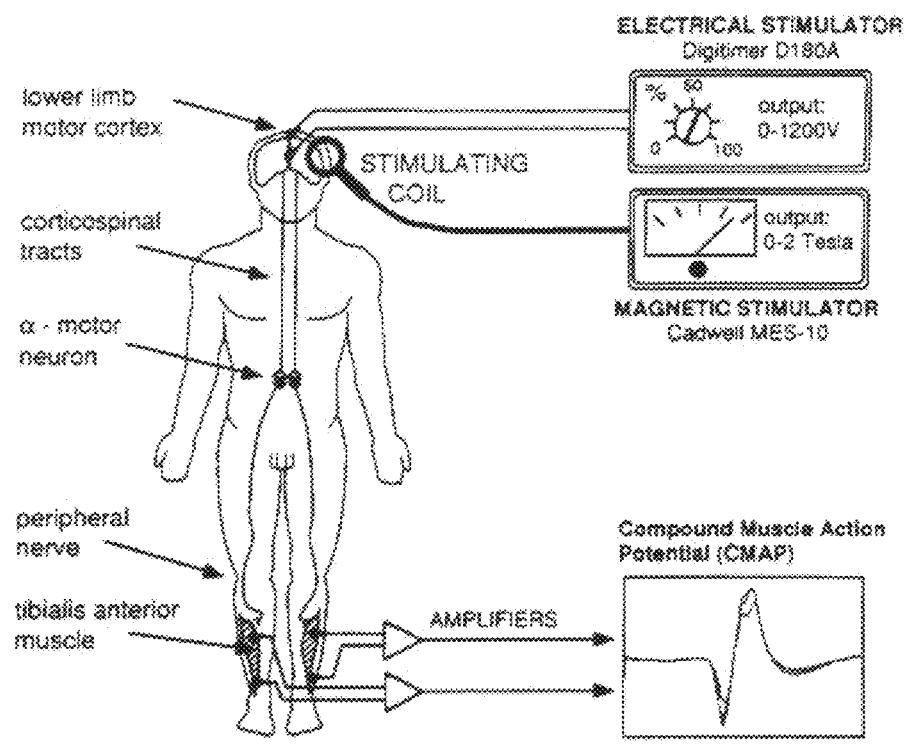
FIG. 2 is a diagram of a patient receiving both magnetic and electric brain stimulation.
Figure 3:
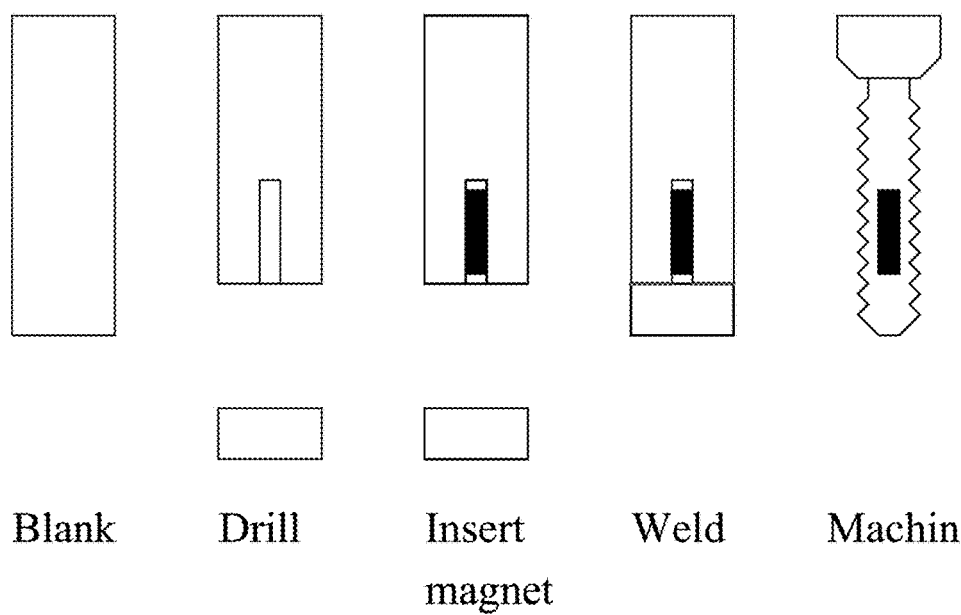
FIG. 3 is an illustration of a skull screw fabrication.

In one embodiment, the skull screw may be shaped after inserting the rod-shaped magnet. This procedure is illustrated in FIG. 3. Here, a hollow core may be drilled into a screw blank. The rod-shaped magnet may then be inserted and enclosed by welding for example, and the skull screw may be machined to a final shape. The magnet may be inserted from the head end or point end of the screw blank, and the magnet insertion and/or welding may be carried out under an inert gas environment. A leak test may be performed to ensure that the magnet has been completely sealed within the skull screw.

In an alternative embodiment, the skull screw is not machined to create a hollow core, but cast with the rod-shaped magnet embedded within the screw.

The head end of the screw may comprise a screw drive such as a Phillips, a slot, a hex, a hex socket, a Torx, a double square, a square, a Robertson, or some other screw drive.

In another embodiment, the skull screw may contain more than one rod-shaped magnet, and these magnets may be arranged with at least one rod-shaped magnet having a north pole pointing towards the head end of the screw and at least one other rod-shaped magnet having a south pole pointing towards the head end of the screw in order to create a multipolar magnetic field with steep magnetic field gradients. In an alternative embodiment, the interior of the skull screw may be filled with a stack of flat magnets. In another alternative embodiment, the skull screw may contain a magnet or magnets with magnetic poles antiparallel to the length of the skull screw. In another alternative embodiment, the skull screw may contain magnets of different diameters and/or lengths so that the shape and strength of the combined magnetic field may be customized.

According again to the first aspect, the implantable magnet assembly also comprises a casing removably attached to the head end of the skull screw, with the casing housing at least one flat magnet, and the at least one flat magnet is arranged substantially perpendicularly with the rod-shaped magnet. As used herein, "flat" refers to a right prism or cylinder shape wherein the largest width of the prism or cylinder is greater than its height. In one embodiment, this flat shape is a disc, meaning a cylindrical flat magnet that has a diameter greater than its height.

In one embodiment, the exterior of the skull screw, or the magnet or magnets in the casing and/or skull screw, may comprise magnetite ($Fe_3O_4$), ferrite alloy (also known as ceramic magnets, such as $BaFe_2O_3$, $BaFe_{12}O_{19}$, $ZnFe_2O_4$, $SrFe_2O_3$, or $SrFe_{12}O_{19}$), neodymium alloy (such as $Nd_2Fe_{14}B$, bonded or sintered), samarium alloy (such as $SmCo_5$, $SmCo_7$, $Sm_2Co_{17}$, $SmFe_7$, $Sm_2Fe_{17}$, $SmCu_7$, $Sm_2Cu_{17}$, $SmZr_7$, $Sm_2Zr_{17}$, $SmHf_7$, $Sm_2Hf_{17}$, $SmPr_7$, or $Sm_2Pr_{17}$), Alnico, or any combination thereof. The magnet or magnets in the casing may comprise different material than the magnet or magnets in the skull screw, but preferably, they comprise the same material, and in a preferred embodiment, the magnets comprise neodymium. The magnets may have a residual flux density ($Br_{max}$) of 0.1-2.0 T, preferably 1.0-1.5 T, more preferably 1.1-1.4 T. The magnets may be plated with nickel or coated with another substance to prevent corrosion. In the embodiment where the exterior of the skull screw comprises a magnetic material, the skull screw may or may not contain an additional rod-shaped magnet.

In one embodiment, the combined magnetic strength of the magnets within the implantable magnet assembly results in a magnetic field strength of 2 mT-15 T, preferably 4 mT-10 T, more preferably 5 mT-5 T as measured from any exterior surface of the implantable magnet assembly. In an alternative embodiment, electromagnets may be used instead of permanent magnets to produce similar magnetic field strengths. In a further embodiment, electromagnets may be used to deliver pulsed magnetic fields.

In one embodiment, the magnet or magnets in the casing have a flat shape, as defined earlier, and may be rectangular prisms, discs, triangular prisms, hexagonal prisms, octagonal prisms, elliptic cylinders, or some other flat shape. The flat magnet or magnets may each have a thickness of 1-100 mm, preferably 3-30 mm, more preferably 3-10 mm, and a largest width of 5-120 mm, preferably 10-60 mm, more preferably 12-40 mm. Preferably, the magnet or magnets in the casing may be discs, and where the casing contains two or more magnets, those magnets may have identical dimensions.

In an alternative embodiment, the magnets in the casing are not flat magnets, but some other shape or shapes, such as prismoids, spheres, toroids, polyhedra, or irregularly-shaped solids. In one alternative embodiment, the magnets in the casing are flat rings of varying inner and outer diameters that allow them to be arranged concentrically with the skull screw and with each other. In another alternative embodiment, rather than being strictly rod-shaped or disc-shaped, the magnet in the skull screw and/or the magnet or magnets in the casing are of a right prism or cylinder shape each with a height equal to its largest width.

Preferably, the flat magnet or flat magnets may be arranged substantially perpendicularly with the rod-shaped magnet. As defined here, "arranged substantially perpendicularly" means that an axis along the length of the rod-shaped magnet intersects at an angle 70-110°, preferably 75-110°, more preferably 80-100° with the geometric planes that contain the two largest faces of the flat magnet, where 90° is a true perpendicular angle. In this arrangement, an extension of an axis along the length of the rod-shaped magnet may or may not intersect with a flat magnet. Furthermore, the rod-shaped magnet may or may not touch a flat magnet. In the case where the rod-shaped magnet does not touch a flat magnet, preferably the shortest distance between them is less than 20 mm, preferably less than 10 mm, more preferably less than 5 mm. Alternatively, in one embodiment, the flat magnet has a hole that accommodates a part of a rod-shaped magnet protruding from the head end of the skull screw and through the casing.

Figure 6A:
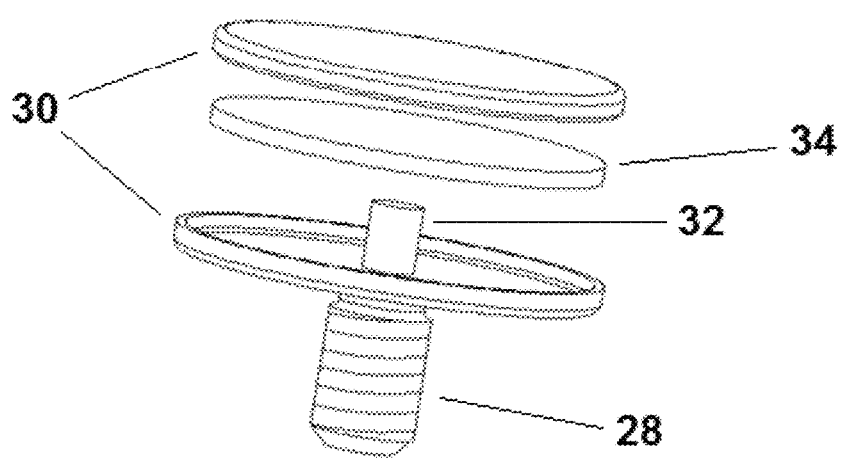
FIG. 6A is an exploded view of an implantable magnet assembly.
Figure 6B:
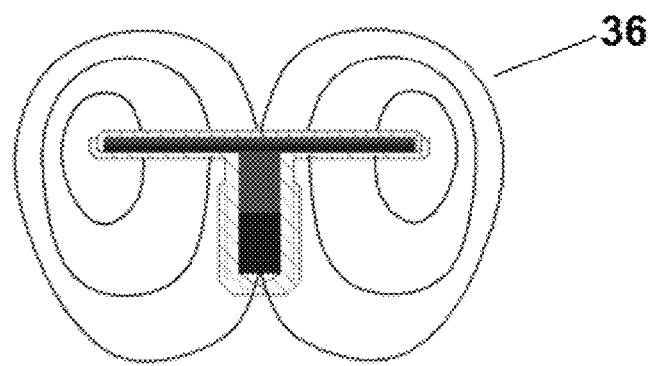
FIG. 6B is a cross-section view of the implantable magnet assembly of FIG. 6A showing the magnetic field lines.

In one embodiment, the implantable magnet assembly has one flat magnet which is cylindrically-shaped and aligned concentrically with the rod-shaped magnet with like magnetic poles of both magnets facing the same direction. By having the magnetic poles of the two magnets facing the same direction, with or without the magnets touching each other, the strength of the magnetic field may be combined and increased, and may penetrate deeper into the brain of a patient. For example, FIG. 6A shows a view of this arrangement that has been expanded along the rotational axis. Here, the rod-shaped magnet 32 from within the skull screw 28 is aligned concentrically with and perpendicular to the disc-shaped magnet 34 housed in the casing 30. FIG. 6B shows a cross-section view of the assembled FIG. 6A with magnetic field lines 36.

In one embodiment, the implantable magnet assembly has at least two flat magnets with edges arranged side-by-side in the casing. The magnets may touch each other, or they may be separated from their nearest neighbor by at most 10 mm, preferably at most 5 mm, more preferably at most 1 mm.

Where two or more flat magnets are housed in the casing, the flat magnets may not be arranged substantially perpendicularly with the rod-shaped magnet, but preferably at least one flat magnet is. In an alternative embodiment, two or more flat magnets housed in the casing may not share the same geometric plane due to the casing being shaped to the curve of a patient's head.

Where two or more flat magnets are housed in the casing, preferably the flat magnets are the same shape, size, and composition, or they may be different. For instance, to create an asymmetric magnetic field, one flat magnet may cover a larger area and/or create a stronger magnetic field. In an alternative embodiment, two or more flat magnets may be stacked within the casing.

In a further embodiment, where the implantable magnet assembly has at least two flat magnets with edges arranged side-by-side in the casing, not every flat magnet is arranged with magnetic poles facing in the same direction. For example, with six flat magnets, three may be arranged with the north pole facing a patient's head, while the other three may be arranged with the south pole facing the patient's head. As another example with six flat magnets, one may be arranged with the north pole facing a patient's head while the other five may be arranged with the south pole facing the patient's head. The magnets may also be arranged with edges side-by-side and with alternating magnetic polarities facing a patient's skull. Such a multipolar arrangement may create steep magnetic field gradients on a patient's brain, which may lead to different brain stimulation outcomes. In a related embodiment, where the flat magnets are rings arranged concentrically with the skull screw, the magnets may alternate polarities.

In another embodiment, where the implantable magnet assembly has at least two flat magnets with edges arranged side-by-side in the casing, all of the flat magnets are arranged with their magnetic poles in the same direction as the magnetic pole of the rod-shaped magnet. For example, where an implantable magnet assembly has the rod-shaped magnet with the north pole pointing towards the center of a patient's brain, and the casing houses six flat magnets, all six flat magnets may have the north pole facing the patient's skull. This arrangement may create an overall stronger magnetic field that may penetrate deeper into the patient's brain.

In one embodiment, the casing may be a flat shape that approximates the shape of the flat magnet or flat magnets contained inside. For example, a disc-shaped magnet may be housed in a disc shaped casing, and two disc-shaped magnets with edges side-by-side may be housed in a FIG. 8 shaped casing. In these embodiments where the casing approximates the shape of the flat magnet or flat magnets, the magnets may be enclosed by a formfitting casing with a thickness from the exterior surface of the magnets of at most 10 mm, preferably at most 5 mm, more preferably at most 3 mm. The casing may have a width or diameter of 8-130 mm, preferably 13-70 mm, more preferably 15-50 mm, and a height of 4-110 mm, preferably 6-40 mm, more preferably 6-20 mm. Preferably, the casing and the flat magnet or magnets contained inside are arranged substantially perpendicularly to the rod-shaped magnet.

In one embodiment, the casing and the skull screw may both comprise the same material, such as a titanium alloy. In another embodiment, the casing may comprise a different material than the skull screw. The casing may be any of the previously mentioned materials suitable for the skull screw, or the casing may be another metal such as nickel and/or aluminum, or another polymeric material such as polylactic acid (PLA), poly(lactic-co-glycolic acid) (PLGA), polyethylene terephthalate (PET), acrylonitrile butadiene styrene (ABS), and/or polytetrafluoroethylene (PTFE), or some other non-metal, such as glass or ceramic. Preferably, the skull screw and the casing are made of the same material. In an alternative embodiment, no casing is present and a flat magnet attaches directly to the head end of the skull screw.

In another embodiment, the casing may be a flat shape but does not approximate the shape of the flat magnet or flat magnets contained inside. For example, two disc-shaped magnets with edges side-by-side may form a FIG. 8 shape by themselves but may be housed in a disc-shaped casing. As another example, a square-shaped flat magnet may be housed in a disc-shaped casing. In this example, the extra volume of the casing may be hollow, composed of the solid casing material, or filled with a cushioning material such as an elastomeric compound. The elastomeric compound may be silicone rubber, latex, butyl rubber, neoprene, and/or nitrile. In addition, the top of the casing may be smoothed to reduce edges and decrease the likelihood of the casing catching on clothing, hats, or helmets.

In one embodiment, the casing may include a cushion on a part of the casing that contacts a patient's head. The part of the casing in contact with a patient's head may entirely comprise a cushion, or only a portion may comprise a cushion, for example, in the form of raised ridges or bumps. Alternatively, the entire exterior surface of the casing, including surfaces that are not in contact with a patient's head, may comprise a cushion. The cushion may comprise an elastomeric compound such as those previously discussed, and may be solid or further comprise air pockets. The cushion may have a height or thickness of 1 mm-4 mm, preferably 1.5-3 mm, more preferably 1.6-2 mm.

In one embodiment, the casing and the head end of the skull screw have a fastening mechanism to removably attach the two. Preferably, the casing can be attached or detached from a skull screw implanted in a patient's head without changing the positioning of the skull screw and without causing discomfort to the patient. In one embodiment, this fastening mechanism may be a bayonet mount, a threaded connector, a clutch, a latch, a key and keyhole, a tongue and groove joint, a snap fastener, an R-clip, a clamp, or any combination thereof. The fastening mechanism may comprise additional parts such as pins, springs, tabs, or levers. The fastening mechanism may reside on the exterior side of the screw near the head end, on the top of the head end of the skull screw, within a recession in the head end of the skull screw, or any combination thereof, with the complementary fastening mechanism located on an exterior surface projecting from the casing, on an interior surface of an indentation of the casing, on an exterior surface flush with the casing, or any combination thereof.

In an alternative embodiment, the magnetic attraction between the magnet in the skull screw and a magnet in the casing may be sufficient to removably attach the casing to the head end of the skull screw. In another alternative embodiment, a plug is used to seal the rod-shaped magnet in the skull screw, as mentioned previously, and this plug may comprise a fastening mechanism to removably attach the casing.

In a related embodiment, the rod-shaped magnet is not sealed inside the skull screw with a plug, but is secured by direct contact with a flat magnet housed in the casing, as shown in FIGS. 6A and 6B.

In another embodiment, the exterior surface of the casing comprises a tab portion, a notch, or a textured surface to facilitate a finger grip. A tab may be in the form of a projection on the surface of the casing while a notch may be in the form of a V-shaped cut. The exterior surface of the casing may be textured with grooves, bumps, knurls, ridges, and/or ribs. A tab, notch, or textured feature may be present in any combination or number on any exterior surface of the casing not in contact with a patient's head. In one embodiment, to facilitate a finger grip, the casing is covered with a cushion of an elastomeric material, such as those listed previously.

In one embodiment, the skull screw and a bottom portion of the casing are machined from a single piece of material. To provide access to either the flat magnet or both flat and rod-shaped magnets, a top portion of the casing may be removably attached to the bottom portion.

In an alternative embodiment, the entire casing may be permanently attached to the head end of the skull screw, and the implantable magnet assembly may be implanted and taken out of a patient's head as one single piece.

In another embodiment, the implantable magnet assembly has a strap with a recess to receive the casing, wherein the strap secures the casing to the head of the patient when worn. Depending on the size and location of the magnet assembly, the strap may reduce discomfort to the patient by decreasing stress and movement on the skull screw. The strap may further cover the edges of the casing so that the casing does not catch on clothing or headwear, as discussed previously. The recess of the strap may be a hole, such as a hole reinforced by a grommet, which may encircle the midsection of the casing. Alternatively, the recess may comprise a depression in the strap thickness, so that the strap covers the top portion of the casing. In an alternative embodiment, the strap may attach to the casing by other means, such as by hooks on the casing. The strap may further comprise a chinstrap to keep the strap from rotating, and a buckle or fastener for taking the strap on or off, and/or changing its tension. The strap may comprise an elastomeric material, such as those listed previously, or may comprise cloth or leather.

The magnets may be secured within the casing by an adhesive, or by a structure inside the casing. This structure may be unmovable, such as a slot or depression, or it may be moveable, such as a clamp or clip. In one embodiment, the casing or a portion of the casing is made of a ferromagnetic material to which the magnets are attracted. In one embodiment, the casing has a top portion removably attached to a bottom portion, and the attachment of the top portion to the bottom portion is sufficient to secure the magnet. In this embodiment, the casing may be opened in order to exchange the magnets. In a further embodiment, the casing may be opened while leaving a bottom portion of the casing still attached to the skull screw.

Figure 7:
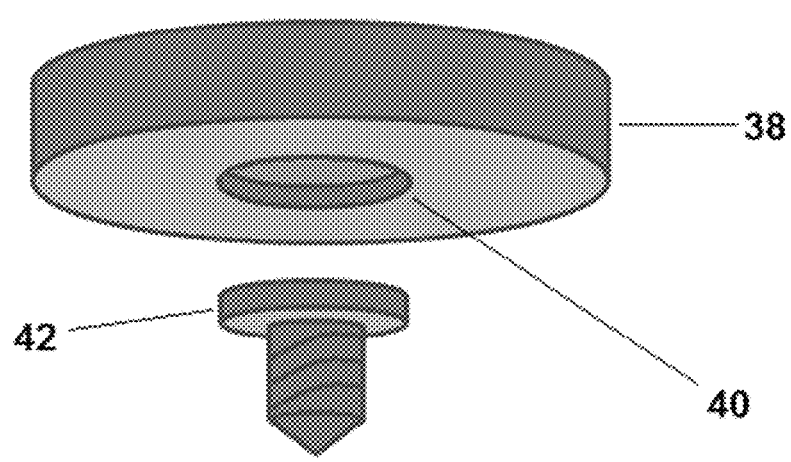
FIG. 7 is an example of an implantable magnet assembly with an indentation in a central portion of the casing.

In one embodiment, the casing may not be entirely flat, but curved to the shape of a person's head. It is possible that once a skull screw location has been determined, a customized casing may be fabricated to better fit the local curve of a patient's head. Likewise, in one embodiment, the casing may comprise an indentation in a central portion of diameter 2.5-12 mm, preferably 5.5-11 mm, more preferably 6-9.5 mm on the side closest to a patient's head in order to receive the skull screw and/or rod-shaped magnet. This indentation may allow the casing to sit on the surface of a patient's scalp. The indentation may be about the size of an unthreaded head section of a skull screw, the portion of a skull screw that protrudes above a patient's scalp, or the size of a rod-shaped magnet protruding above the head end of a skull screw. The indentation depth may be 1-10 mm, preferably 2-8 mm, more preferably 3-7 mm. The indentation may go through the bottom portion of the casing partway, or it may go through entirely as a hole in the casing that exposes the flat magnet. FIG. 7 shows a casing 38 with an indentation 40 that goes partway through the casing to receive the unthreaded head section 42 of a skull screw. In one embodiment where the rod-shaped magnet protrudes above the head end of the skull screw and the indentation is a hole in the casing, the rod-shaped magnet may contact the flat magnet. In another related embodiment, where the flat magnet has a hole, a hole in the casing allows the rod-shaped magnet to stick into the flat magnet. In another embodiment, the interior sides of the indentation may contain a fastening mechanism to removably attach to the head end of the skull screw.

According to a second aspect, the present disclosure relates to a method of delivering a static magnetic field to a patient's brain by implanting the implantable magnet assembly, in one or more of its embodiments, into the patient's skull where the skull screw traverses the skull with the point end located at the interior surface of the skull and the head end located at the exterior surface of the skull. The magnetic field may produce neuronal excitatory and/or inhibitory effects by changing the polarity of different neurons. The reverse polarity of the magnetic field may or may not produce the same effects on a patient's brain. Different magnetic implant locations, as well as the shape, strength, and polarity of the magnetic fields, may lead to different treatment options. In one embodiment, a patient's brain may first be imaged by MRI, positron emission tomography (PET) and/or computed tomography (CT) to better determine these parameters.

The implanting step may require surgery under anesthesia, and may involve shaving a portion of the patient's head and cutting a segment of the scalp to expose an exterior portion of the skull. Depending on the design of the skull screw, a hole or incision in the patient's skull may be required. In one embodiment, the entire implantable magnet assembly may be inserted as one piece into a patient's skull. In a preferred embodiment, where the implantable magnet assembly comprises a casing removably attached to the skull screw, the skull screw may be implanted first, and then the casing may be attached. Alternatively, the skull screw may be inserted first, and then after a period of healing for the skull and scalp, the casing may be attached. A surgeon may use a powered orthopedic screwdriver to insert the skull screw or implantable magnet assembly, or may use non-powered surgical hand tools. Preferably, the skull screw is inserted substantially perpendicularly to the skull surface. In a preferred embodiment the skull screw is not implanted to a depth that would perturb or harm the patient's brain tissue. In a related embodiment, the diameter of the skull screw unthreaded head section and length of the shaft section are chosen so that the skull screw point end cannot penetrate far into the cranial cavity. For example, the length of the skull screw shaft section may be at most 9 mm, preferably at most 8 mm, more preferably at most 7 mm, and the unthreaded head section may have a diameter at least 1 mm, preferably at least 2 mm greater than the core diameter of the skull screw.

In an alternative embodiment, the skull screw may be inserted sufficiently deep to anchor to the skull without puncturing the interior surface of the skull bone. In another alternative embodiment, instead of implanting the assembly directly into the skull, a receptacle for the screw is implanted into a patient's head, and the implantable magnet assembly is inserted into the receptacle. In another alternative embodiment, a hole is drilled into a patient's skull and an unthreaded skull screw is inserted and secured by osseointegration with the bone tissue. In another alternative embodiment, where the rod-shaped magnet is inserted after implanting the skull screw, the hollow core of the skull screw may be used as a screw drive.

In one embodiment of the method, the static magnetic field is delivered for more than 2 hours. Preferably the static magnetic field may be delivered for more than one week, preferably more than four weeks. To deliver the static magnetic field for a certain amount of time, the implantable magnet assembly is left in place for that time period. Given the secure design of the implantable magnet assembly, the delivery of the static magnetic field may occur on an outpatient basis, meaning that a patient may not require constant medical supervision nor have to significantly restrain his or her lifestyle. Alternatively, types of psychological or medical evaluation may be performed during the time period of magnetic field delivery in order to detail the effects of the treatment. These evaluations may be questionnaires, blood tests, vital signs, electroencephalography (EEG), electrocardiography (ECG/EKG), or brain imaging. In addition, other therapies may coincide with the period of magnetic stimulation, such as chemotherapy, psychological counseling, or further brain stimulation with pulsed magnetic fields, electromagnetic fields, or electric currents.

In a further embodiment of the method, the method additionally involves removing the casing while leaving the rod-shaped magnet and skull screw in place and attaching a second casing with at least one second flat magnet, wherein the at least one second flat magnet applies a magnetic field that differs from the magnetic field produced by the at least one flat magnet. Evaluations of a patient with the implantable magnet assembly may warrant changes to the magnetic field strength or shape. This may be accomplished by exchanging the casing for a second casing that may deliver a different static magnetic field. In one embodiment, the casing may be exchanged by a physician without using specialized tools. In a related alternative embodiment, mentioned previously, a top portion of the casing may be opened in order to exchange, remove, and/or add magnets without separating the entire casing from the implanted skull screw.

Figure 8:
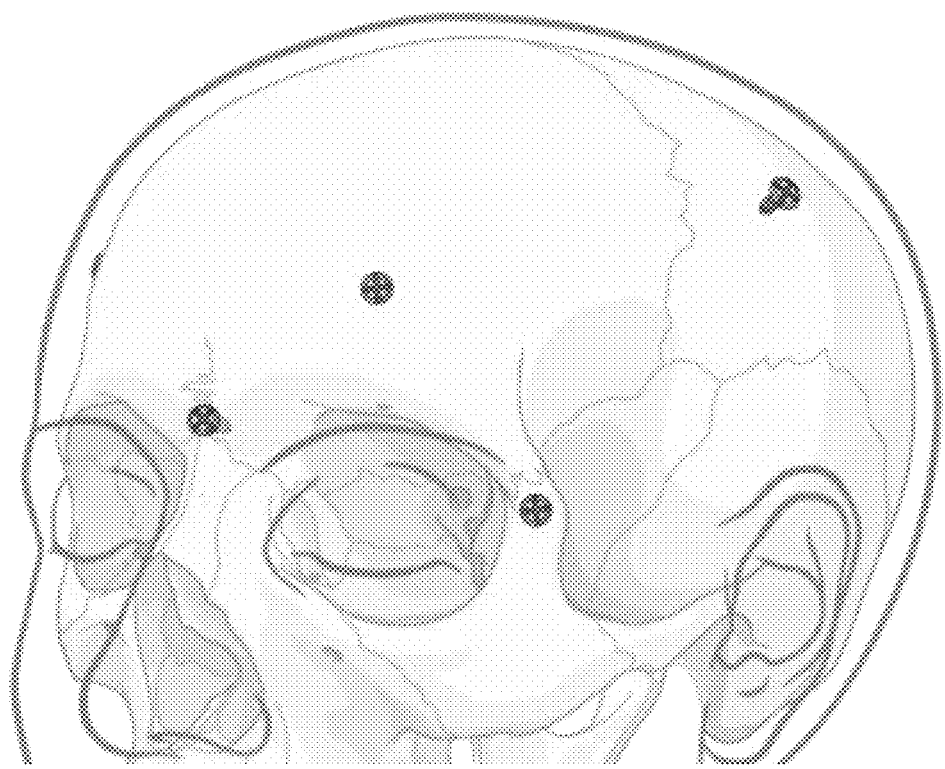
FIG. 8 is an illustration of a patient's skull implanted with multiple magnet-containing skull screws.

Following the required course of treatment, the magnets or the entire implantable assembly may be removed from the patient. In an alternative embodiment, more than one magnet assembly may be implanted into a patient's head. For example, FIG. 8 shows an illustration of a patient's skull with more than one skull screw implanted. These assemblies may be implanted or removed at the same medical appointment, or at different appointments. The more than one magnet assembly may each produce magnetic fields of the same shape and strength, or they may produce different magnetic fields. For implantable magnetic assemblies on directly opposing sides of a patient's head, the magnetic polarities of all the magnets may be aligned in one direction, for example, the north poles of the magnets may all point towards the left side of the patient. Such an arrangement may create a unipolar magnetic field through the center of the patient's brain. Alternatively, implantable magnetic assemblies on opposing sides of a patient's head may contain magnets where the poles are not all aligned in a single direction.

In one embodiment of the method, the cognitive performance of the patient is increased relative to a second patient not receiving a magnetic field from a magnet or an electromagnet. Magnetic fields may increase neurological activity in areas of the brain leading to an increased aptitude in pattern recognition, working memory, arithmetic, attention span, long-term memory, creativity, and language. The aptitude of the patients may be compared through cognitive testing, such as visual search testing, dual n-back, Stanford-Binet Intelligence Scales, Raven's Progressive Matrices, Naglieri Nonverbal Ability Test, Controlled Oral Word Association Test, or Wechsler Intelligence Scales.

In one embodiment of the method, a patient has a brain tumor and/or a neurological ailment, and the brain tumor or neurological ailment of the patient is treated by the static magnetic field from the implantable magnet assembly. As used herein, to "treat" a brain tumor or a neurological ailment means to reduce or inhibit the progression, severity, and/or duration of the brain tumor or neurological ailment or other accompanying symptoms. As mentioned previously, another form of therapy may be combined with the magnetic stimulation, such as chemotherapy in the case of a brain tumor.

In one embodiment of the method, where a neurological ailment is treated, the neurological ailment is epilepsy, migraine, depression, anxiety, attention deficit disorder, hyperactivity, bipolar disorder, stroke, dementia, schizophrenia, delirium, neurosis, psychosis, Parkinson's disease, alcohol withdrawal, drug withdrawal, dizziness, motion sickness, insomnia, dystonia, chronic pain, obsessive compulsive disorder, Tourette's syndrome, essential tremor, spasticity, trigeminal neuralgia, and/or headache. Preferably the neurological ailment is epilepsy, headache, depression, anxiety, attention deficit disorder, bipolar disorder, dementia, schizophrenia, delirium, neurosis, psychosis, Parkinson's disease, dizziness, and/or motion sickness. More preferably the neurological ailment is epilepsy, headache, depression, anxiety, bipolar disorder, dementia, schizophrenia, delirium, neurosis, psychosis and/or Parkinson's disease. It is possible for a patient to present more than one neurological ailment and receive therapy for those neurological ailments from a single implantable magnet assembly. For example, a patient may receive the magnetic stimulation as therapy for both headache and anxiety.

In an alternative embodiment, the skull screw and the casing contain no magnets, in order to serve as a placebo for magnetic stimulation. In this embodiment, the skull screw and the casing may contain rod-shaped and flat-shaped pieces of material, such as a non-magnetic metal, in order to approximate the shape and density of the magnets being replaced. With this type of placebo assembly, a patient's head may be implanted with the placebo and evaluated. Alternatively, the patient with the placebo may be compared to a patient or patients with a magnet-containing assembly of similar appearance. Alternatively, a patient's head may be implanted with two or more assemblies, with at least one containing magnets and at least one as a magnet-free placebo.

In a related embodiment of the implantable magnet assembly, the skull screw may contain no magnets, while the casing contains at least one flat magnet.

According to a third aspect, the present disclosure relates to a method of treating a patient's brain with a static magnetic field by implanting the skull screw containing the rod-shaped magnet, but not attaching the casing or flat magnets. Here, the skull screw may appear as FIG. 5A, which does not have an unthreaded head section at its head end 24 and may not have an attachment mechanism to removably attach a casing. The magnet may be sealed under the head end of the screw, and the screw drive may be any of those previously listed. For example, FIG. 5A shows a Frearson screw drive at the head end. Embodiments describing the dimensions, materials, features, fabrication, and insertion of the skull screw without a flat magnet are similar to what was mentioned previously.

In one embodiment of this method, a patient may have a brain tumor and/or a neurological ailment, and the brain tumor and/or neurological ailment is treated. The neurological ailment may be any one or a combination of those previously listed, and the methods of treatment are similar to what was mentioned previously for the implantable magnet assembly comprising at least one flat magnet. In another embodiment, for patients not receiving therapy for a brain tumor or neurological ailment, the cognitive performance of the patient may be increased relative to a second patient not receiving a magnetic field from a magnet or an electromagnet, as has been discussed previously.

The examples below are intended to further illustrate the construction of the implantable magnet assembly and methods of use and are not intended to limit the scope of the claims.

Example 1

Constructing a Magnet-Loaded Skull Screw

A magnetic skull screw may be machined from titanium by the following procedure, which is summarized in FIG. 3:
1. Start with a titanium rod material cut to an appropriate length as a screw blank.
2. Remove a cap section from the blank.
3. Drill an axial hole at the tip end of the screw blank where the magnet will be inserted.
4. Insert and secure the magnet in the axial hole.
5. Weld the cap into the body of the screw under inert gas and special cooling. Perform a leak test using a helium mass spectrometer.
6. Machine the screw to its final shape. Perform a leak test using a helium mass spectrometer.
7. Finish the surface by anodizing, texturing, or ion implant.

Example 2

Shape of the Magnetic Field

Figure 9:
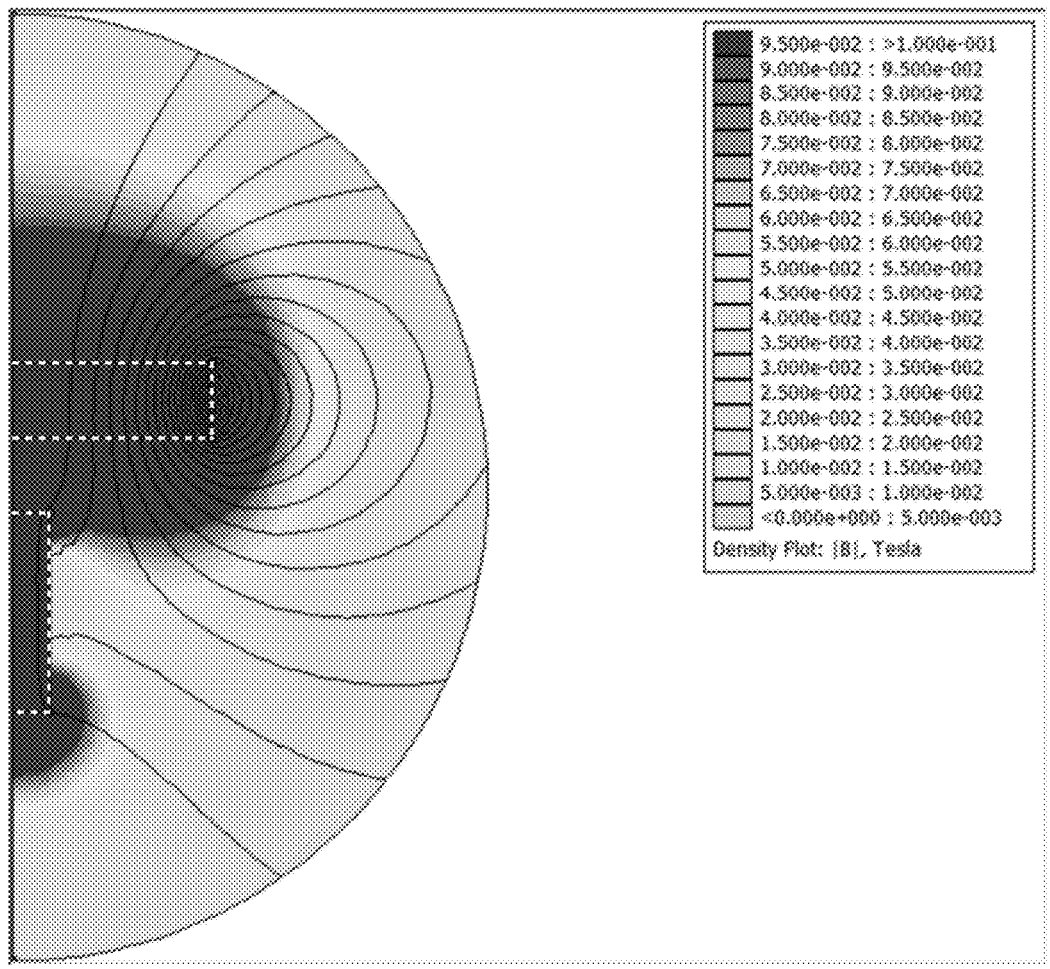
FIG. 9 is a simulated magnetic field of two magnets arranged as if within an implantable magnet assembly.

One half of a simulated absolute magnetic field strength from two magnets is shown in FIG. 9. The arrangement and shape of the magnets, which are outlined by the dotted lines, approximates those in the implantable magnet assembly: the top magnet is a disc-shaped magnet, and the bottom magnet is a cylindrical rod-shaped magnet, with the left side of the plot being the rotational axis of symmetry for both magnets. Magnetic field lines are also shown. To reduce artifacts, the simulation assumes the magnets to be in free space, rather than housed within an assembly. The lowest magnetic field strength represented is about 100 times stronger than the Earth's magnetic field.

Example 3

Strength of the Magnetic Field from the Magnet-Loaded Skull Screw

Figure 10:
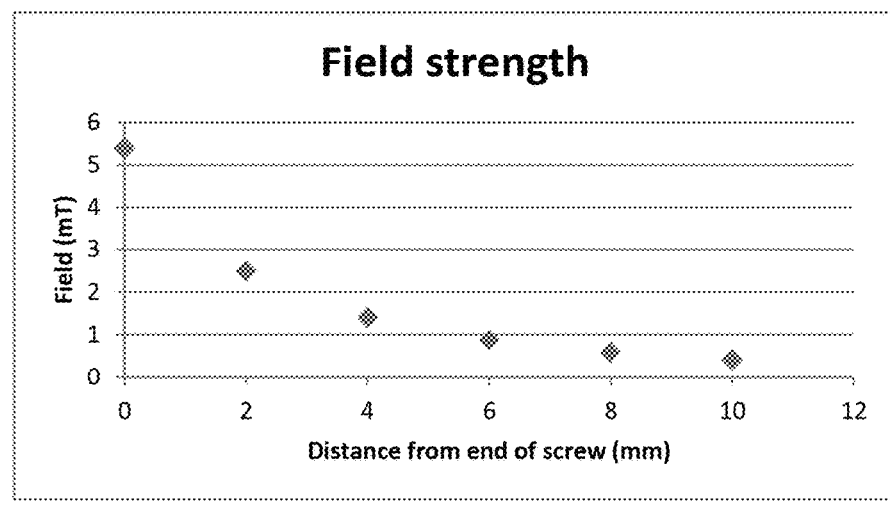
FIG. 10 is a plot of the magnetic field strength at certain distances from a magnet-loaded skull screw.

The magnetic field near the tip of the skull screw is solenoidal in geometry and depends on a number of parameters. The axial field strength was calculated for the following parameters and assumptions:
a) Screw length: 40 mm
b) Screw diameter: 7 mm
c) Magnet material: NdFeB, $Br_{max}$ (residual flux density) =1.2 T
d) Magnet dimensions: 8 mm long, 1.5 mm diameter
e) Magnet to tip spacing: 5 mm These parameters produce a magnetic strength along the axis from the tip of the screw as shown in FIG. 10. It is useful to compare these values with the magnetic field of the Earth. The magnetic field strength at the surface of the Earth varies considerably but averages about 0.04 mT. As FIG. 10 shows, the magnetic field 1 cm from the tip of the magnet-loaded skull screw is about 150 times larger than that of the Earth.

The magnetic field strength near either end of the magnet, but off axis, is expected to be of similar magnitude to the axial values. Additionally, larger diameter magnets may be used to increase the magnetic field strength. For instance, if the diameter of the magnet is increased from 1.5 mm to 3 mm, the magnetic field strengths represented in FIG. 10 will increase by a factor of 4.

Example 4

Figure 11:
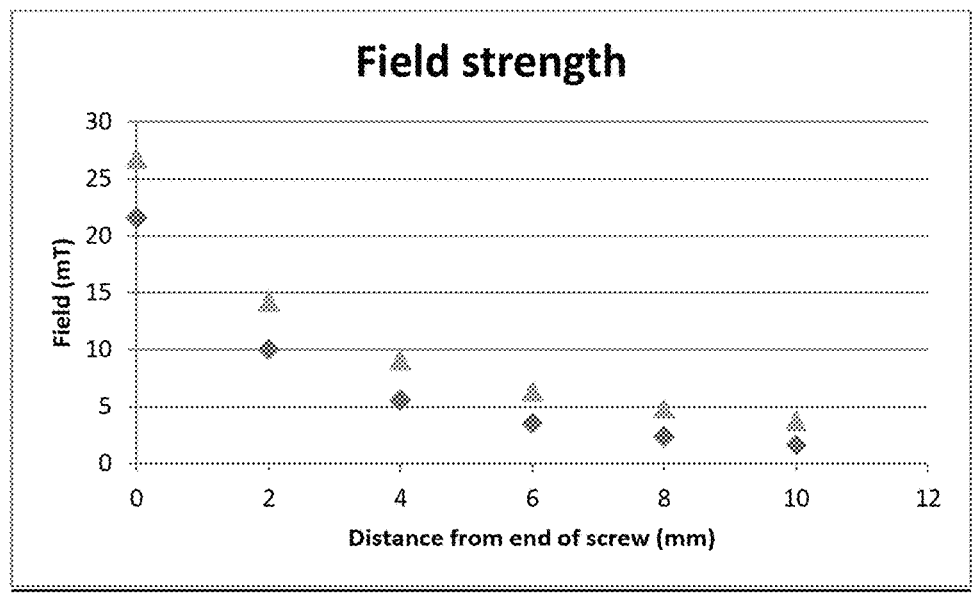
FIG. 11 is a plot of the magnetic field strength at certain distances from the tip of an implantable magnet assembly, showing the contribution of the flat magnet.

Strength of the Magnetic Field from the Combined Disc-Shaped Magnet and Rod-Shaped Magnet A flat, disc-shaped magnet can be secured to the head end of the magnet-loaded skull screw as in FIG. 6A, creating a mushroom-shaped magnetic field, as shown in FIG. 6B and FIG. 9. For another simulation of the magnetic field strength from the tip of the skull screw, a disc-shaped magnet with a 16 mm diameter and 3 mm height is attached to the head end of the skull screw, which contains a rod-shaped magnet 8 mm long and 3 mm in diameter. FIG. 11 shows the magnetic field strength of this arrangement from the tip of the skull screw. The diamonds show the magnetic field strength from only the rod-shaped magnet. The triangles show the combined magnetic field strength from both magnets. The disc-shaped magnet does not contribute significant magnetic field strength at the tip of the skull screw, since it is farther away. The magnetic field from the disc-shaped magnet is much stronger in the region just under the head end of the skull screw. For example, 8 mm below the disc-shaped magnet (an area expected to be just under the skull bone), the field is about 60 mT, falling to the levels shown in the chart as the distance from the disc-shaped magnet increases.

The invention claimed is:

1. An implantable magnet assembly, comprising:
 a rod-shaped magnet housed within a skull screw, wherein the skull screw has a head end and a point end and is configured to traverse a patient's skull with the point end located at an interior surface of the skull and the head end located at an exterior surface of the skull;
 a casing removably attached to the head end of the skill screw, and
 at least two flat magnets housed in the casing, with edges of the magnets arranged side-by-side;
 wherein the rod-shaped magnet and the at least two flat magnets are arranged substantially perpendicularly.

2. The implantable magnet assembly of claim 1 which emits a magnetic field with a magnetic field strength of 2 mT-15 T as measured on an exterior surface of the implantable magnet assembly.

3. The implantable magnet assembly of claim 1, wherein not every flat magnet is arranged with magnetic poles facing in the same direction.

4. The implantable magnet assembly of claim 1, wherein the at least two flat magnets are arranged with magnetic poles in the same direction, and the direction of the poles of the at least two flat magnets are arranged in the same direction as a magnetic pole of the rod-shaped magnet.

5. The implantable magnet assembly of claim 1, wherein an exterior of the skull screw comprises at least one selected from the group consisting of titaniumn, titanium alloy, stainless steel, cobalt alloy, magnetite, ferrite alloy, neodymium alloy, samarium alloy, Alnico, carbon fiber, polyethylene, polymethylmethacrylate, polyether ether ketone, and polycarbonate.

6. The implantable magnet assembly of claim 1, wherein an exterior surface of the casing comprises a tab portion, a notch, or a textured surface to facilitate a finger grip.

7. The implantable magnet assembly of claim 1, wherein a central portion of the casing on a side of the casing configured to be closest to the patient's head comprises an indentation to receive the head end of the skull screw.

8. An implantable magnet assembly, comprising:
 a rod-shaped magnet housed within a skull screw, wherein the skull screw has a head end and a point end and is configured to traverse a patient's skull with the point end located at an interior surface of the skull and the head end located at an exterior surface of the skull;
 a casing removably attached to the head end of the skull screw; and
 at least one flat magnet housed in the casing:
 wherein the rod-shaped magnet and the at least one flat magnet are arranged substantially perpendicularly, and
 wherein the casing is removably attached to the head end of the skull screw by a fastening mechanism selected from the group consisting of a bayonet mount, a threaded connector, a clutch, a latch, a key and keyhole, a tongue and groove joint, a snap fastener, an R-clip, and a clamp.

9. The implantable magnet assembly of claim 8, further comprising a strap with a recess to receive the casing, wherein the strap is configured to secure the casing in place when encircling a part of a head of the patient.

10. The implantable magnet assembly of claim 8, further comprising a cushion disposed on a bottom portion of the casing that receives the head end of the skull screw to cushion a head of the patient.

11. A method of delivering a static magnetic field to a brain of a patient comprising:
 implanting the implantable magnet assembly of claim 1 into the patient's skull,
 wherein the skull screw traverses the patient's skull with the point end located at the interior surface of the skull and the head end located at the exterior surface of the skull;
 removing the casing while leaving the rod-shaped magnet and skull screw in place; and
 attaching a second casing comprising at least one additional flat magnet,
 wherein the at least one additional flat magnet applies a second magnetic field that differs from a magnetic field produced by the at least two flat magnets.

12. The method of claim 11 wherein the static magnetic field is delivered for more than 2 hours.

13. The method of claim 11 wherein a cognitive performance of the patient is increased relative to a second patient not receiving a magnetic field from a magnet or an electromagnet.

14. The method of claim 11 wherein the patient has a brain tumor and/or a neurological ailment, and the brain tumor and/or neurological ailment is treated.

15. The method of claim 14, wherein the patient has at least one neurological ailment selected from the group consisting of epilepsy, migraine, depression, anxiety, attention deficit disorder, hyperactivity, bipolar disorder, stroke, dementia, schizophrenia, delirium, neurosis, psychosis, Parkinson's disease, alcohol withdrawal, drug withdrawal, dizziness, motion sickness, insomnia, dystonia, chronic pain, obsessive compulsive disorder, Tourette's syndrome, essential tremor, spasticity, trigeminal neuralgia, and headache.

* * * * *